United States Patent [19]

Eberlein et al.

[11] Patent Number: 5,175,158
[45] Date of Patent: Dec. 29, 1992

[54] CONDENSED DIAZEPINONES, PROCESSES FOR PREPARING THEM AND PHARMACEUTICAL COMPOSITIONS CONTAINING THESE COMPOUNDS

[75] Inventors: Wolfgang Eberlein; Wolfhard Engel, both of Biberach; Gunter Trummlitz, Warthausen; Gerhard Mihm; Norbert Mayer, both of Biberach; Henri Doods, Warthausen, all of Fed. Rep. of Germany

[73] Assignee: Dr. Karl Thomae, GmbH, Biberach an der Riss, Fed. Rep. of Germany

[21] Appl. No.: 261,950

[22] Filed: Oct. 24, 1988

[30] Foreign Application Priority Data

Oct. 23, 1987 [DE] Fed. Rep. of Germany ....... 3735895

[51] Int. Cl.⁵ .................. A61K 31/55; C07D 243/10
[52] U.S. Cl. .................................. 514/220; 540/495
[58] Field of Search ...................... 540/495; 514/220

[56] References Cited

FOREIGN PATENT DOCUMENTS 3235795 3/1984 Fed. Rep. of Germany ...... 540/495

Primary Examiner—Johann Richter
Attorney, Agent, or Firm—D. E. Frankhouser; M. M. Timbers; A. R. Stempel

[57] ABSTRACT

New diazepinones of formula I

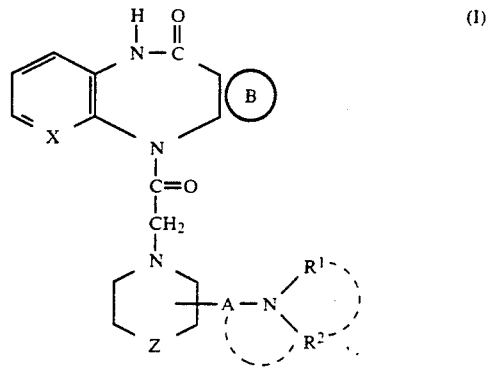

wherein the substituents are defined herein,
which compounds exhibit favorable effects on heart rate and in view of the absence of inhibitory effects on gastric acid secretion and salivation and the absence of mydriatic effects, are suitable as vagal pacemakers for the treatment of bradycardia and bradyarrhythmia in human and veterinary medicine.

9 Claims, No Drawings

CONDENSED DIAZEPINONES, PROCESSES FOR PREPARING THEM AND PHARMACEUTICAL COMPOSITIONS CONTAINING THESE COMPOUNDS

The invention relates to new condensed diazepinones, processes for preparing them and pharmaceutical compositions containing these compounds.

Condensed diazepinones with anti-ulcerative properties and an inhibitory effect on gastric juice secretion are already known from EP-A-0 039 519 and 0 057 428 and from U.S. Pat. Nos. 3,660,380; 3,691,159; 4,213,984; 4,213,985; 4,210,648; 4,410,527; 4,424,225; 4,424,222 and 4,424,226.

EP-A-0 156 191 (U.S. Pat. No. 4,550,107) describes how for condensed diazepinones completely different, valuable pharmacological properties compared with the compounds of the above-mentioned publications can be induced by introducing new aminoacyl groups. The condensed diazepinones according to the invention surprisingly are distinguished from these compounds by a substantially more powerful effect and resorption after oral administration, whilst having a comparable or better selectivity.

The new condensed diazepinones have the general formula I,

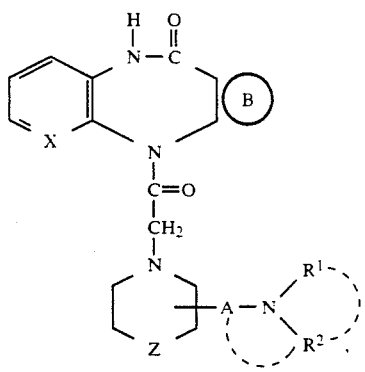

wherein Ⓑ represents one of the divalent groups

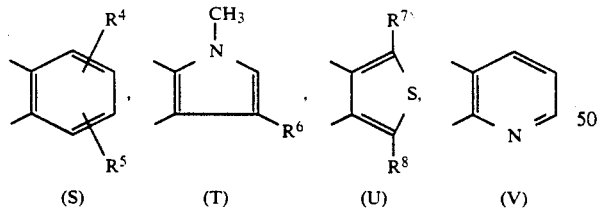

and A, X, Z, $R^1$, $R^2$ and $R^4$ to $R^8$ are defined as follows:

X is a =CH— group or a nitrogen atom,

A is a straight-chained or branched saturated alkylene group with 3 to 7 carbon atoms which may also be interrupted by an oxygen or sulphur atom or the group >NR3, wherein R3 is an alkyl group with 1 to 3 carbon atoms, Z is a single bond, an oxygen or sulphur atom, a methylene or 1,2-ethylene group, $R^1$ is a branched or unbranched alkyl group with 1 to 7 carbon atoms, a cycloalkyl or (cycloalkyl)alkyl group with a total of up to 8 carbon atoms, an aralkyl group with up to 9 carbon atoms optionally substituted by a fluorine, chlorine or bromine atom and/or by a methyl, methoxy or trifluoromethyl group, an aliphatic acyl group with up to 7 carbon atoms or a benzoyl group optionally substituted by a fluorine, chlorine or bromine atom and/or by a methyl, methoxy or trifluoromethyl group, $R^2$ represents a branched or unbranched alkyl group with 1 to 6 carbon atoms, but $R^2$ may also be a hydrogen atom if $R^1$ represents the above-mentioned aliphatic acyl group or optionally substituted benzoyl group, $R^1$ and $R^2$ may also, together with the nitrogen atom between them, represent a saturated, monocyclic 5-, 6- or 7-membered ring which optionally may also be substituted by an aminocarbonyl, dimethylaminocarbonyl or diethylaminocarbonyl group and/or may be interrupted by an oxygen atom, $R^2$ may also, however, be linked to a carbon atom of the A chain in such a way that, together with the group $NR^1$, a saturated 5-, 6- or 7-membered heterocyclic ring is formed, $R^4$ and $R^5$, which may be identical or different, represent a hydrogen, fluorine, chlorine or bromine atom or an alkyl group with 1 to 4 carbon atoms, $R^6$ is a hydrogen or chlorine atom or a methyl group, $R^7$ and $R^8$, which may be identical or different, represent hydrogen atoms or alkyl groups with 1 to 4 carbon atoms, but $R^8$ may also represent a halogen atom.

Preferred compounds of general formula I above are those wherein the group

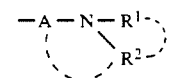

is in the 3- or 4- position of the saturated heterocyclic group and

A represents a straight-chained or branched alkylene group with 3 to 5 carbon atoms which may optionally be interrupted by the group >N—$CH_3$, X represents a nitrogen atom or a =CH— group, Ⓑ represents the divalent group (S) or (U), wherein $R^4$ and $R^5$ represent hydrogen atoms, $R^7$ and $R^8$ represent hydrogen atoms or one of these groups represents the methyl group, $R^1$ and $R^2$, which may be identical or different, represent alkyl groups with 1 to 3 carbon atoms or together with the nitrogen atom between them represent the 1-piperidinyl group or $R^2$ together with the corresponding carbon atom of the group —A— represents the 4-piperidinyl group of formula

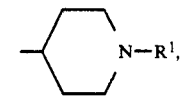

wherein $R^1$ represents a lower alkyl group with 1 to 3 carbon atoms and Z represents a methylene group.

The cycloalkyl group may be, for example, a cyclobutyl, cyclopentyl, cyclohexyl or cycloheptyl group whilst the (cycloalkyl)alkyl group may be, for example, a cyclopentyl- or cyclohexyl- methyl or -ethyl group. The optionally substituted aralkyl group for $R^1$ may be, for example: a benzyl group, a 2-phenylethyl group, a 3-phenylpropyl group, these groups optionally being substituted in the 2- or 4-position of the phenyl group by a fluorine, chlorine or bromine atom and/or by a methyl, methoxy or trifluoromethyl group. Examples of aliphatic acyl groups for $R^1$ include, in particular, the acetyl, propionyl and butyryl groups.

After being reacted with inorganic or organic acids the compounds of general formula I may also occur in the form of their physiologically acceptable salts. Suitable acids include, for example, hydrochloric, hydrobromic, sulphuric, methylsulphuric, phosphoric, tartaric, fumaric, citric, maleic, succinic, gluconic, malic, p-toluenesulphonic, methanesulphonic and amidosulphonic acids.

To illustrate the object of the invention, the following compounds may be mentioned by way of example:

5,11-dihydro-11-[[4-[4-(1-piperidinyl)butyl]-1-piperidinyl]-acetyl]-6H-pyrido[2,3-b][1,4]benzodiazepin-6-one 5,11-dihydro-11-[[4-[3-(1-methyl-4-piperidinyl)propyl]-1-piperidinyl]acetyl]-6H-pyrido[2,3-b] [1,4]benzodiazepin- 6-one 5,11-dihydro-11-[[4-[3-(1-piperidinyl)propyl]-1-piperidinyl]- acetyl]-6H-pyrido[2,3-b][1,4]benzodiazepin-6-one 4,9-dihydro-3-methyl-4-[[4-[3-(1-piperidinyl)propyl]-1-piperidinyl]acetyl]-10H-thieno[3,4-b][1,5]benzodiazepin- 10-one According to the invention, the new base substituted condensed diazepinones of general formula I are obtained by the following processes:

a) Base substituted condensed diazepinones of general formula Ia

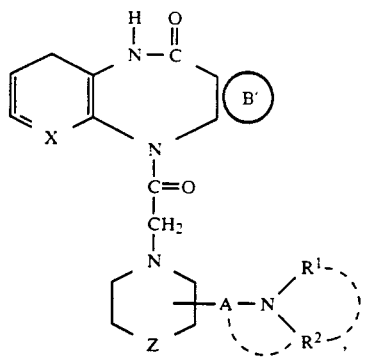

(Ia)

wherein X, Z, A and $R^1$ and $R^2$ are defined as hereinbefore and ' represents one of the divalent groups (S), (U), (V) or (T')

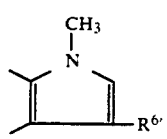

(T')

wherein $R^{6'}$ is a chlorine atom or a methyl group, are obtained by reacting haloacyl compounds of general formula II

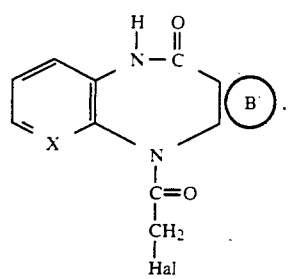

(II)

wherein X and ' are as hereinbefore defined and Hal represents a c bromine or iodine atom, with secondary amines of general formula III

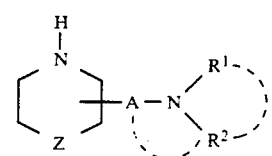

(III)

wherein A, Z, $R^1$ and $R^2$ are as hereinbefore defined.

The amination is effected in an inert solvent at temperatures of between $-10°$ C. and the boiling temperature of the solvent, preferably either with at least 2 moles of secondary amine of general formula III or with 1 to 2 moles of a secondary amine of general formula III and an auxiliary base. Suitable solvents include, for example, chlorinated hydrocarbons such as methylene chloride, chloroform or dichloroethane; open-chained or cyclic ethers such as diethylether, tetrahydrofuran or dioxan; aromatic hydrocarbons such as benzene, toluene, xylene, chlorobenzene or pyridine; alcohols such as ethanol or isopropanol; ketones such as acetone; acetonitrile, dimethylformamide or 1,3-dimethyl-2-imidazolidinone. Examples of auxiliary bases include tertiary organic bases such as triethylamine, N-methylpiperidine, diethylaniline, pyridine and 4-(dimethylamino)pyridine or inorganic bases such as alkali metal or alkaline earth metal carbonates or hydrogen carbonates, hydroxides or oxides. If desired, the reaction may be accelerated by the addition of alkali metal iodides. The reaction times range from 15 minutes to 80 hours depending on the nature and quantity of the amine of general formula III used.

b) The same base substituted condensed diazepinones of general formula Ia may also be obtained by acylating diazepinones of general formula IV,

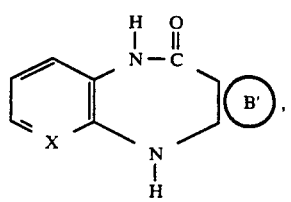

(IV)

wherein X and ' are defined as hereinbefore, with carboxylic acid derivatives of general formula V

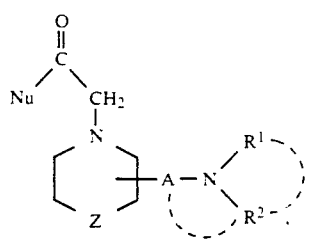

(V)

wherein Z, A, $R^1$ and $R^2$ are defined as hereinbefore and Nu represents a nucleofugic group or leaving group.

The reaction of the compounds of general formula IV with the acid derivatives of general formula V is effected in a manner known per se. The leaving group Nu is a group which, together with the carbonyl group to which it is bound, forms a reactive carboxylic acid derivative. Examples of reactive carboxylic acid derivatives include acid halides, esters, anhydrides or mixed anhydrides such as those obtained from salts of the corresponding acids (Nu=OH) and acid chlorides, such as phosphorus oxide chloride, diphosphoric acid tetrachloride or chloroformic acid esters or the N-alkyl-2-acyloxypyridinium salts formed when compounds of general formula V (Nu=OH) are reacted with N-alkyl-2-halopyridinium salts.

The reaction is preferably carried out with the mixed anhydrides of strong inorganic acids, particularly dichlorophosphoric acid. The reaction is optionally carried out in the presence of an acid-binding agent (proton acceptor). Suitable proton acceptors include, for example, alkali metal carbonates or hydrogen carbonates such as sodium carbonate or potassium hydrogen carbonate; tertiary organic amines such as pyridine, triethylamine, ethyldiisopropylamine, 4-(dimethylamino)-pyridine or sodium hydride. The reaction is carried out at temperatures of between $-25°$ C. and $130°$ C. in an inert solvent. Examples of inert solvents include chlorinated aliphatic hydrocarbons such as methylene chloride and 1,2-dichloroethane; open-chained or cyclic ethers such as diethylether, tetrahydrofuran or 1,4-dioxan; aromatic hydrocarbons such as benzene, toluene, xylene and o-dichlorobenzene; polar aprotic solvents such as acetonitrile, dimethylformamide or hexamethylphosphoric acid triamide; or mixtures thereof. The reaction times range from 15 minutes to 80 hours depending on the nature and quantity of the acylating agent of general formula V used. It is not necessary to prepare the compounds of general formula V in pure form; indeed, they may be produced in situ in the reaction mixture in known manner.

c) The new pyrrolo-condensed diazepinones of general formula Ib covered by general formula I,

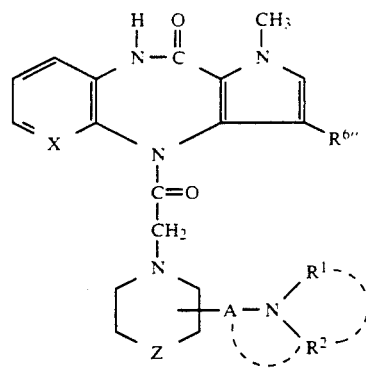

(Ib)

wherein

X, Z, A, $R^1$ and $R^2$ are defined as hereinbefore, $R^{6''}$ represents a hydrogen atom, may be obtained by hydrogenolysis from compounds of general formula Ib wherein $R^6$ represents a chlorine atom.

The hydrogenolysis is carried out in the presence of catalysts of metals of the VIIIth sub-group of the periodic table of elements, for example palladium on animal charcoal, palladium on barium sulphate, Raney nickel or Raney cobalt, and under hydrogen pressures of from 1 to 300 bar and temperatures of $0°$ C. to $130°$ C. in the presence of solvents, e.g. alcohols such as methanol or ethanol; ethers such as dioxan, tetrahydrofuran; carboxylic acids, for example acetic acid; or tertiary amines, for example triethylamine. If the process is carried out in the absence of additional hydrogen chloride acceptors, for example sodium carbonate, potassium hydrogen carbonate, triethylamine or sodium acetate, the hydrochlorides of the desired compounds are obtained directly and may be isolated after removal of the catalyst by evaporation of the reaction solution. If in the above-mentioned hydrogenolysis reaction the hydrogen is replaced by formic acid, the reaction will in principle take place even under unpressurised conditions. In this variant, it has proved particularly useful to carry out the reaction with formic acid in the presence of dimethylformamide as solvent and palladium on charcoal as catalyst at temperatures of between $70°$ and $110°$ C. and to carry out the reduction with triethylammonium formate in the presence of excess triethylamine and palladium on animal charcoal or palladium acetate and triarylphosphines such as triphenylphosphine, tris-(o-tolyl)phosphine, tris-(2,5-diisopropylphenyl)phosphine, at temperatures of between $40°$ and $110°$ C.

Bases of general formula I thus obtained may subsequently be converted into the acid addition salts thereof or, if acid addition salts are obtained, they may be converted into the free bases or other pharmacologically acceptable acid addition salts.

The basically substituted condensed 6H-pyrido[2,3-b]-[1,4]benzodiazepin-6-ones of general formula I according to the invention, particularly when Ⓑ represents the divalent group (U) and the group

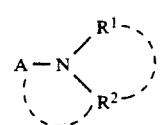

is in the 2- or 3- position of the saturated heterocyclic ring, contains up to three independent chiral elements, of which up to two are asymmetric carbon atoms in the side chain. The acylated tricyclic group itself may be regarded as a further chiral element, which may occur in two mirror image forms. It depends on the nature of the tricyclic group whether the energy barrier for inversion at this centre is so high that the individual isomers are stable at ambient temperature and capable of being isolated. It has been found that, in compounds of general formula I wherein X is a nitrogen atom and the positions adjacent to the diazepinone ring are unsubstituted, the activating energy required is reduced to such an extent that diastereoisomers can no longer be detected at ambient temperature, let alone preparatively isolated.

The amino acylated condensed diazepinones of general formula I according to the invention thus contain up to three chirality elements, one of which is not structurally stable at ambient temperature under certain circumstances. Such compounds may therefore occur in several diastereoisomeric forms and/or as enantiomeric (+) and (−) forms. The invention includes the individual isomers as well as the mixtures thereof. The diastereoisomers in question may be separated on the basis of their different physico-chemical properties, e.g. by fractional recrystallisation from suitable solvents, by high pressure liquid chromatography, column chromatography or gas chromatography.

The separation of any racemates of the compounds of general formula I may be carried out by known methods, for example using an optically active acid such as (+) or (−) tartaric acid or a derivative thereof such as (+) or (−) diacetyltartaric acid, (+) or (−) monomethyltartrate or (+) camphorsulphonic acid.

According to a conventional method of isomer separation, the racemate of a compound of general formula I is reacted in equimolar amounts with one of the above-mentioned optically active acids in a solvent and the crystalline diastereomeric salts obtained are separated by making use of their different solubilities. This reaction may be carried out in any type of solvent provided that it shows sufficient differences in solubility of the salts. Preferably, methanol, ethanol or mixtures thereof are used, e.g. in a ratio by volume of 50:50. Each of the diastereomeric salts is then dissolved in water, neutralised with a base such as sodium carbonate or potassium carbonate and in this way the corresponding free compound is obtained in the (+) or (−) form.

Only one enantiomer or a mixture of two optically active diastereomeric compounds covered by general formula I is obtained if the methods of synthesis described above are carried out with only one enantiomer of general formula III or V.

In order to prepare the haloacyl compounds of general formula II the starting compounds of general formula IV

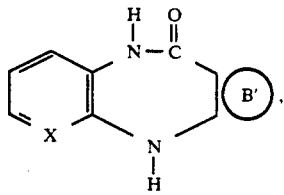

(IV)

are reacted with compounds of general formula Hal—CH$_2$CO— Hal' (VII) or [Hal—CH$_2$—CO]$_2$O (VIII), wherein Hal' has one of the meanings of Hal and Hal is defined as hereinbefore. This acylation is carried out without or preferably in the presence of an inert solvent at ambient temperature or elevated temperature, at most at the boiling temperature of the solvent, optionally in the presence of an auxiliary base and/or an acylation catalyst. The acid halides of general formula VII are preferred to the acid anhydrides of general formula VIII. The preferred acid halide of general formula VII is chloroacetylchloride whilst the preferred acid anhydride of general formula VIII is chloroacetic acid anhydride. Examples of solvents include aromatic hydrocarbons such as toluene, xylene or chlorobenzene; open-chained or cyclic ethers such as diisopropylether or dioxan; chlorinated hydrocarbons such as dichloroethane; other solvents such as pyridine, acetonitrile or dimethylformamide. Examples of auxiliary bases include tertiary organic bases such as triethylamine and ethyl diisopropylamine or pyridine; or inorganic bases such as anhydrous alkali metal or alkaline earth metal carbonates or hydrogen carbonates or alkaline earth metal oxides. Examples of acylation catalysts include imidazole, pyridine and 4-dimethylaminopyridine.

If in a compound of general formula II Hal represents a chlorine atom, this may easily be replaced by the more reactive iodine by reaction with sodium iodide in acetone or ethanol (in connection with this, reference is made to U.S. Pat. No. 4,550,107).

Intermediate compounds of general formula III which have an alkylene group A interrupted in the beta-position relative to the saturated heterocycle by a heteroatom may be synthesised analogously to the methods discussed in detail in DE-A-36 26 095.

Intermediate compounds of general formula III wherein Z represents a methylene group are conveniently prepared from correspondingly substituted pyridines, for example by catalytic hydrogenation in ethanolic/hydrochloric acid solution and using platinum(IV) oxide as catalyst (see also F. F. Blicke et al., J. Org. Chemistry 26, 3258 (1961)) or in glacial acetic acid and in the presence of platinum(IV)oxide (see also W. F. Minor et al., J. Med. Pharm. Chem. 5, 96, 105 ff. (1962) and A. H. Sommers et al., J. Amer. Chem. Soc. 75, 57, 58 ff. (1953)). The substituted pyridines may in turn easily be synthesised by methods familiar to those skilled in the art, e.g. by the addition of corresponding secondary amines, dialkylaminoalkanols or dialkylaminoalkanethiols to vinyl pyridines, by reduction of suitable pyridine alkanoic acid amides with lithium aluminium hydride, by alkylation of picolines with dialkylaminoalkylhalides in the presence of lithium diisopropylamide or sodium amide (see also A. E. Tschitschibabin, Bull. Soc. Chim. France 1938, 436) or by reacting (omega-haloalkyl)-pyridines with dialkylaminoalkanols, dialkylaminoalkanethiols or secondary amines (see also L. Rondahl, Acta Pharm. Suec. 13, 229-34 (1976)) or the metallised derivatives thereof.

A generally applicable method of synthesising amines of general formula III consists in reducing suitable heterocyclically substituted alkane carboxylic acid dialkylamides which are optionally interrupted by heteroatoms in the alkylene group, for example using lithium aluminium hydride. Any protecting groups still present from the preliminary stages and occurring on the nitrogen function of the saturated heterocycle may subsequently be split off in the usual way; a benzyl group may, for example, be split off by hydrogenolysis in the presence of palladium/animal charcoal. For example, 5-oxo-2-pyrrolidine acetic acid (G. L. Evans et al., J. Amer. Chem. Soc., 72, 2727 (1950)) may be reacted successively with thionyl chloride and a dialkylamine of interest and the resulting N,N-dialkyl-5-oxo-2-pyrrolidinoacetamide may subsequently be reduced with lithium aluminium hydride to yield the desired 2-[2-(dialkylamino)-ethyl]pyrrolidine; or the 4-benzyl-3-(chloromethyl)-morpholine hydrochloride obtainable from 4-benzyl-3-(hydroxymethyl)-morpholine (G. R. Brown et al., J. Chem. Soc. Perkin Trans. I 1985, 2577) by the action of thionyl chloride may be converted into (4-benzyl-3-morpholinyl)alkanoic acids by chain lengthening in the usual way and thus be used for the synthesis of 3-(dialkylaminoalkyl)morpholines.

The compounds of general formula III, wherein $R^2$ is linked to the corresponding carbon atom of the group —A— to form a 4-piperidinyl group, may be obtained, for example, by reacting a compound of general formula

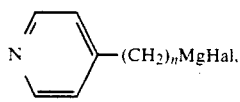

wherein n represents the number 1 to 4, with a compound of general formula

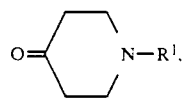

wherein $R^1$ is defined as hereinbefore; whereby, after the water has been removed, one of the two isomers of general formula

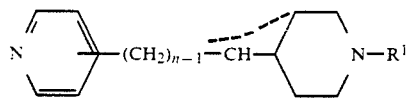

or a mixture thereof is obtained which is subsequently hydrogenated in the presence of platinum dioxide as catalyst in acetic acid to yield the desired diamine.

The starting compounds of general formula V wherein Nu represents an alkoxy group may be obtained by reacting diamines of general formula III with haloacetic acid esters, optionally using additional auxiliary bases, e.g. triethylamine, or catalysts, e.g. Triton B. By saponification of the resulting esters, e.g. with barium hydroxide solution, the carboxylic acids coming under general formula V are obtained which may be used to prepare derivatives with other nucleofugic groups.

The invention further relates to pharmaceutical compositions containing one or more condensed diazepinones of general formula I or the physiologically acceptable salts thereof.

For this purpose, the compounds of general formula I may be incorporated, in known manner, in the conventional pharmaceutical preparations, e.g. solutions, suppositories, tablets, coated tablets, capsules or infusions. The daily dosage is generally between 0.02 and 5 mg/kg, preferably 0.02 and 2.5 mg/kg, more particularly 0.05 and 1.0 mg/kg of body weight, preferably administered in the form of several, preferably 1 to 3, individual doses, to achieve the desired results.

The base substituted condensed diazepinones of general formula I and the acid addition salts thereof have valuable properties; in particular, they have favourable effects on heart rate and, owing to their lack of mydriatic effects and inhibitory effects on gastric acid secretion and salivation, they are suitable for use as vagal pacemakers for treating bradycardia and bradyarrhythmia in human and veterinary medicine; some of the compounds also have spasmolytic properties on peripheral organs, particularly the colon and bladder.

A favourable relation between tachycardiac effects on the one hand and on the other hand the undesirable effects on pupil size and the secretion of tears, saliva and gastric acid which occur in therapeutic agents with an anticholinergic component is of particular importance in the therapeutic use of the substances. The following tests show that the compounds according to the invention show surprisingly good relations of this kind.

A. STUDIES OF BINDING TO MUSCARINIC RECEPTORS

In vitro measurement of the $IC_{50}$ value

The organs were donated by male Sprague-Dawley rats weighing 180–220 g. After the heart and submandibular gland and cerebral cortex had been removed, all other steps were carried out in ice cold Hepes HCl buffer (pH 7.4; 100 millimolar NaCl, 10 millimolar $MgCl_2$). The whole heart was cut up with scissors. All the organs were then homogenised in a Potter apparatus.

For the binding test the homogenised organs were diluted as follows:

| | |
|---|---|
| Whole heart | 1 : 400 |
| Cerebral cortex | 1 : 3000 |
| Submandibular gland | 1 : 400 |

The homogenised organs were incubated at a certain concentration of the radioaligned and at a series of concentrations of the non-radioactive test substances in an Eppendorf centrifuge tube at 30° C. Incubation lasted 45 minutes. The radioligand used was 0.3 nanomolar $^3$H-N-methylscopolamine ($^3$H-NMS). Incubation was ended by the addition of ice cold buffer followed by vacuum filtration. The filters were rinsed with cold buffer and their radioactivity was determined. It represents the sum of specific and non-specific binding of $^3$H-NMS. The proportion of non-specific binding was defined as the radioactivity which was bound in the presence of 1 micromolar quinuclidinylbenzylate. Each measurement was taken four times. The $IC_{50}$ values of the non-labelled test substances were determined graphically. They represent that concentration of test substance at which the specific binding of $^3$H-NMS to the muscarinic receptors in the various organs was inhibited by 50%. The results can be seen from Table 1.

B. INVESTIGATION OF FUNCTIONAL SELECTIVITY OF THE ANTIMUSCARINIC EFFECT

Substances with antimuscarinic properties inhibit the effects of agonists supplied exogenically or of acetylcholine, which is released from cholinergic nerve endings. The following is a description of some methods that are suitable for the detection of cardioselective antimuscarinic agents.

"In vivo" methods

The objective of the methods was to confirm the selectivity of the antimuscarinic effect. Those substances which had been selected on the basis of "in vitro" tests were tested for their
1. $M_1/M_2$ selectivity in the rat,
2. Salivation-inhibiting effect on the rat and
3. Inhibition of the acetylcholine effect on the bladder, bronchi and heart rate in the guinea pig.

1. $M_1/M_2$ Selectivity in the Rat

The method used was described by Hammer and Giachetti (Life Sciences 31, 2991-2998 (1982)). 5 minutes after the intravenous injection of increasing doses of the substance, either the right vagus was electrically stimulated (frequency: 25 Hz; pulse width: 2 ms; duration of stimulus: 30s; voltage: supramaximal) or 0.3 mg/kg of McN-A-343 were intravenously injected into male THOM rats. The bradycardia caused by vagus stimulation and the rise in blood pressure caused by McN-A-343 were determined. The dosage of the substances which reduced either the vagal bradycardia ($M_2$) or the rise in blood pressure ($M_1$) by 50% was determined graphically. For the results see Table II.

2. Salivation-Inhibiting Effect in the Rat

Using the method of Lavy and Mulder (Arch int. pharmacodyn. 178, 437-445, (1969)) male THOM rats anaesthetised with 1.2 g/kg of urethane were given increasing doses of the substance by i.v. route. The secretion of saliva was initiated by subcutaneous administration of 2 mg/kg of pilocarpine. The saliva was absorbed with blotting paper and the surface area covered was measured every 5 minutes by planimetry. The dosage of the substance which reduced the volume of saliva by 50% was determined graphically. For the results see Table II.

3. Inhibition of the Effect of Acetylcholine on the Bladder, Bronchi and Heart Rate in Guinea Pigs 5 minutes after the administration of the test substance, 10 microgram/kg of acetylcholine were simultaneously injected intravenously and intra-arterially into anaesthetised guinea pigs. The heart rate was recorded directly by extracorporeal derivation of the ECG, the expiration resistance according to Konzett-Rossler and contraction of the exposed bladder. In order to determine the inhibition of the acetylcholine activity on the organs under investigation, dosage/activity curves were recorded and from them $-\log ED_{50}$ values were determined. For the results see Table III. The following compounds for example were investigated as described above:

A = 4,9-dihydro-3-methyl-4-[[4-[3-(1-piperidinyl)-propyl]-1-piperidinyl]acetyl]-10H-thieno[3,4-b][1,5]benzodiazepin-10-one, B = 5,11-dihydro-11-[[4-[3-(1-piperidinyl)propyl]-1-piperidinyl]acetyl]-6H -pyrido[2,3-b][1,4]benzodiazepin-6-one, C = 5,11-dihydro-11-[[4-[4-(1-piperidinyl)butyl]-1-piperidinyl]acetyl]-6H -pyrido[2,3-b][1,4]benzodiazepin-6-one, D = 5,11 dihydro-11-[[4-[3-(1-methyl-4-piperidinyl)-propyl]-1-piperidinyl]acetyl]-6H-pyrido[2,3-b][1,4]-benzodiazepin-6-one, and as comparison substances E = 11-[[2-[(diethylamino)methyl]-1-piperidinyl]acetyl]-5,11-dihydro-6H-pyrido [2,3-b][1,4]benzodiazepin-6-one (see U.S. Pat. No. 4,550,107)

F = 5,11-dihydro-11-[(4-methyl-1-piperazinyl)acetyl]-6H-pyrido[2,3-b][1,4]benzodiazepin-6-one (pirenzepine, see U.S. Pat. No. 3,660,380) and G = atropine.

TABLE I

Receptor Binding Tests in vitro: Results:

| Substance | Receptor Binding Tests $IC_{50}$ [nMl$^{-1}$] | | |
|---|---|---|---|
| | Cortex | Heart | Submandibular gland |
| A | 60 | 5 | 200 |
| B | 200 | 20 | 550 |
| C | 50 | 9 | 200 |
| D | 500 | 50 | 1500 |
| E | 1200 | 140 | 5000 |
| F | 100 | 1500 | 200 |
| G | 2 | 4 | 4 |

The information shown in Table I above shows that the new compounds of general formula I distinguish between muscarinic receptors in different tissues. This is clear from the substantially lower $IC_{50}$ values when the test substances are investigated on preparations from the heart compared with those from the cerebral cortex and submandibular gland.

TABLE II $M_1/M_2$ selectivity and salivation-inhibiting activity on rat: Results:

| Substance | $-\log ED_{50}$ [Mkg$^{-1}$] | | |
|---|---|---|---|
| | Heart | Blood pressure | Salivation |
| A | 7.14 | 5.82 | 5.20 |
| B | | | |
| C | 6.94 | 5.42 | <4.5 |
| D | | | |
| E | 6.42 | 5.63 | 5.00 |
| F | 5.60 | 6.94 | 6.22 |
| G | 7.94 | 7.34 | 7.60 |

TABLE III

Inhibition of acetylcholine activity on the bladder, bronchi and heart rate in the guinea pig: Results:

| Substance | $-\log ED_{50}$ [Molkg$^{-1}$] | | |
|---|---|---|---|
| | Heart | Bronchi | Bladder |
| A | 6.91 | 6.55 | 5.56 |
| B | 6.91 | 6.33 | 5.74 |
| C | 7.06 | 6.18 | 5.58 |
| D | 6.45 | 6.07 | <5.0 |
| E | 5.84 | 5.58 | 4.73 |
| F | 5.85 | 6.57 | 5.36 |
| G | 7.70 | 7.96 | 7.03 |

The pharmacological data in Tables II and III above show—in total agreement with the receptor binding studies—that the heart rate is increased by the above-mentioned compounds even at dosages at which there is no restriction in the secretion of saliva.

Moreover, the pharmacological data in Table III above indicate a surprisingly high power of distinction between the heart and smooth muscle.

The above-mentioned substances show a substantially improved effectiveness compared with the known compound E. At the same time, their therapeutically useful selectivity is retained. This results in a reduction in the quantity of drug to be administered to the patient without increasing the risk of muscarinic side effects.

Furthermore, the compounds prepared according to the invention are well tolerated; even in the highest doses administered, no toxic side effects were observed in the pharmacological trials.

The following Examples are intended to illustrate the invention:

EXAMPLE 1

5,11-Dihydro-11-[4-4-(1-piperidinyl)butyl]-1-piperidinyl -acetyl]-6H-pyrido2,3-b ][1,4]benzodiazepin-6-one A mixture of 5.32 g (0.018 mol) of 11-(chloroacetyl)-5,11-dihydro-6H-pyrido[2,3-b][1,4]benzodiazepin-6-one, 150 ml of acetonitrile, 4.02 g (0.018 mol) of 4-[4-(1-piperidinyl) butyl]piperidine and 1.93 g (0.019 mol) of triethylamine is refluxed for 3 hours with stirring. After cooling, it is evaporated to dryness in vacuo. The residue is digested in saturated potassium carbonate solution, and two phases are formed. The organic phase is separated off in a separating funnel and the aqueous phase is extracted several times with ethyl acetate. The combined organic extracts are washed out several times with saturated sodium chloride solution, filtered over activated charcoal and, after being dried over sodium sulphate, evaporated down in vacuo. The residue is chromatographed on silica gel using a mixture of methylene chloride/cyclohexane/methanol/ethyl acetate/ammonia (750:57:57:195:7.5 v:v:v:v:v) as eluant.

After the corresponding fractions have been evaporated down, an eluate residue is obtained which is recrystallised from ethyl acetate/ethanol. Colourless crystals are obtained, m.p. 228°–229° C. Yield: 3.8 g (45% of theory).

EXAMPLE 2

5,11-Dihydro-11-[[4-[3-(1-methyl-4-piperidinyl)propyl]-1-piperidinyl]acetyl]6H -pyrido[2,3-b][1,4]benzodiazepin- 6-one Prepared analogously to Example 1 from 11-(chloroacetyl)-5,11-dihydro-6H-pyrido[2,3-b][1,4benzodiazepin-6-one and 4-[3-(1-methyl-4-piperidinyl)-propyl]piperidine, but using dimethylformamide instead of acetonitrile as solvent, in a yield of 20% of theory. Colourless crystals, m.p. 192°–194° C. (isopropanol/diisopropylether).

EXAMPLE 3

5,11-Dihydro-11-[[4-[3-(1-piperidinyl)propyl]-1-piperidinyl]-acetyl]-6H-pyrido [2,3-b][1,4]benzodiazepin-6-one Prepared analogously to Example 1 from 11-(chloroacetyl)-5,11-dihydro-6H-pyrido[2,3-b][1,4]benzodiazepin-6-one and 4-[3-(1-piperidinyl)propyl]piperidine in a yield of 87% of theory.
Colourless crystals, m.p. 202°–203° C. (ethyl acetate).

EXAMPLE 4

6,11-Dihydro-11-[[4-[4-(1-piperidinyl)butyl]-1-piperidinyl]-acetyl]-5H-pyrido [2,3-b][1,5]benzodiazepin-5-one Prepared analogously to Example 1 from 11-(chloroacetyl)-6,11-dihydro-5H-pyrido[2,3-b][1,5]benzodiazepin-5-one and 4-[4-(1-piperidinyl)butyl]piperidine in a yield of 37% of theory.
Colourless crystals, m.p. 167°–168° C.

$C_{28}H_{37}N_5O_2$ (475.64):
Calculated: C, 70.71; H, 7.84; N, 14.72.
Found: C, 70.44; H, 7.75; N, 14.65.

EXAMPLE 5

11-[[4-[4-(Diethylamino)butyl -1-piperidinyl]acetyl]-6,11-dihydro-5H-pyrido[2,3-b][1,5]benzodiazepin-5- one Prepared analogously to Example 1 from 11-(chloroacetyl)-6,11-dihydro-5H-pyrido[2,3-b][1,5]benzodiazepin-5- one and 4-[4-(diethylamino)butyl]piperidine in a yield of 24% of theory.
Colourless crystals, m.p. 147°–148° C. (ethyl acetate).
$C_{27}H_{37}N_5O_2$ (463.63):
Calculated: C, 69.95; H, 8.04; N, 15.11.
Found: C, 69.62; H, 7.89; N, 15.18.

EXAMPLE 6

4-[[4-(4-Diethylamino)butyl -1-piperidinyl]acetyl]-4,9-dihydro-3-methyl-10H-thieno [3,4-b][1,5]benzodiazepin- 10-one Prepared analogously to Example 1 from 4-(chloroacetyl)-4,9-dihydro-3-methyl-10H-thieno [3,4-b][1,5]benzodiazepin-10-one and 4-[4-(diethylamino)-butyl]piperidine in a yield of 58% of theory.
Colourless crystals, m.p. 192°–194° C.

EXAMPLE 7

11-[[2-[3-(Diethylamino)propyl]-1-piperidinyl]acetyl]-5,11-dihydro-6H-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 2-[3-(diethylamino)propyl]piperidine in a yield of 74% of theory.
Colourless crystals, m.p. 151°–153° C. (acetonitrile).

EXAMPLE 8

5,11-Dihydro-11-[[3-[3-[4-(aminocarbonyl)-1-piperidinyl]-propyl]-1-piperidinyl]acetyl]-6H-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 3-[3-[4-(aminocarbonyl)-1-piperidinyl]propyl]- piperidine, but using dimethylformamide instead of acetonitrile as solvent, in a yield of 33% of theory.
IR ($CH_2Cl_2$): 1670 $cm^{-1}$ (C=O);
$^1$H-NMR ($CDCl_3/CD_3OD$, 400 MHz):
delta 8.30 (br.,s, 1H); 7.95 (br.,s, 1H); 7.65 (m, $^3$H); 7.50 (m, 1H); 7.40 (m, 1H); 3.65–3.35 (m, 2H); 3.30–2.90
(m, 3H); 2.75 (br.,s, 1H); 2.50–2.15 (m, 4H); 2.15–1.30
(m,13H); 1.10 (br.,s, 3H); 0.75 (m, 1H).
MS: M+ 504 m/e (molecular weight calculated as 504.644 g/mol).

EXAMPLE 9

5,11-Dihydro-11-[[2-[3-(dimethylamino)propyl]-1piperidinyl]acetyl]-6H-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 2-[3-(dimethylamino)propyl]piperidine in a yield of 25% of theory.
Colourless crystals, m.p. 174°–176° C. (acetonitrile).

EXAMPLE 10

11-[[2-[4-(Diethylamino)butyl]-1-piperidinyl]acetyl]-5,11-dihydro-6-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 2-[4-(diethylamino)butyl]piperidine in a yield of 54% of theory.

Colourless crystals, m.p. 149°–150° C. (ethyl acetate).

EXAMPLE 11

5,11-Dihydro-11-[[2-[4-(dimethylamino)butyl-1-piperidinyl]-acetyl]-6H-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 2-[4-(dimethylamino)butyl]piperidine in a yield of 25% of theory.

Colourless crystals, m.p. 157°–159° C. (ethyl acetate).

EXAMPLE 12

5,11-Dihydro-11-[[3-[3-(dimethylamino)propyl]-1-piperidinyl]acetyl]-6H-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 3-[3-(dimethylamino)propyl]-piperidine in a yield of 7% of theory.

RF 0 35 (Merck prepared TLC plates, silica gel F254; eluant: dichloromethane/methanol/conc. ammonia 90/10/1)

IR (CH$_2$Cl$_2$): 1665 cm$^{-1}$ (C=O), 1680 cm$^{-1}$ (C=O);
$^1$H-NMR (DMSO-d$_6$/CD$_3$OD, 80 MHz): delta : 8.2 (d, 1H); 8.0–7.2 (m~6H); 4.0–2.2 (m, 8H); 2.15 (d, 6H, N(CH$_3$)$_2$); 2.0–0.6 (m~9H).

EXAMPLE 13

5,11-Dihydro-11-[[4-(1-methyl-4-piperidinyl)-1-piperidinyl]acetyl]-6H-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 4-(1-methyl-4-piperidinyl)piperidine in a yield of 23% of theory.

Colourless crystals, m.p. 208°–211° C. (ethyl acetate).

EXAMPLE 14

5,11-Dihydro-11-[[2-(1-methyl-4-piperidinyl)-1-piperidinyl]acetyl]-6H-pyrido[2,3-b]]1,4]benzodiazepin-6-one Prepared analogously to Example 1 from 11-(chloroacetyl)-5,11-dihydro-6H-pyrido[2,3-b][1,4]benzodiazepin-6-one and 2-(1-methyl-4-piperidinyl)piperidine in a yield of 27% of theory.

Colourless crystals <m.p. 172°–173° C. (diisopropylether).

EXAMPLE 15

5,11-Dihydro-11-[[2-[4-(1-piperidinyl)butyl]-1-piperidinyl]acetyl]-6H-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 2-[4-(1-piperidinyl)butyl]piperidine in a yield of 42% of theory.

Colourless crystals, m.p. 144°–145° C. (acetonitrile).

EXAMPLE 16

11-[[3-[4-[(Benzoyl)methylamino]butyl]-1-piperidinyl]-acetyl]-5,11-dihydro-6H-pyrido[2,3-b][1,4]benzodiazepin-6-one-hydrochloride Prepared analogously to Example 1 from 11-(chloroacetyl)-5,11-dihydro-6H-pyrido[2,3-b][1,4]benzodiazepin-6-one and the base in ethyl acetate and adding ethereal hydrochloric acid the hydrochloride was obtained in a yield of 62%.

IR (CH$_2$Cl$_2$): 1630 cm$^{-1}$; 1670–1700 cm$^{-1}$ (C=O); 1H-NMR (DMSO-d6; 400 MHz): delta : 11.1 (s, 1H); 8.35 (d, 1H); 8.0–7.3 (m, 11H); 4.7–4.4 (m, 1H); 4.1–3.9 (br.,s, 1H); 3.8–2.5 (m,~10H); 2.0–0.8 (m,~10H).

EXAMPLE 17

5,11-Dihydro-11-[[3-[4-[(2-phenylethyl)methylamino]-butyl]-1-piperidinyl]acetyl]-6H-pyrido[2,3-b][1,4]benzodiazepin-6-one Prepared analogously to Example 1 but using dimethyl-formamide instead of acetonitrile as solvent, from 11-(chloroacetyl)-5,11-dihydro-6H-pyrido[2,3-b][1,4]benzodiazepin-6-one and 3-[4-[(2-phenylethyl)-methylamino]-butyl]piperidine in a yield of 46% of theory.

Colourless crystals, m.p. 154°–155° C. (ethyl acetate).

EXAMPLE 18

11-[[3-[4-[(Acetyl)methylamino]butyl-1-piperidinyl]-acetyl]-5,11-dihydro-6H-pyrido[2,3-b][1,4]benzodiazepin-6-one-hydrochloride Prepared analogously to Example 1 from 11-(chloroacetyl)-5,11-dihydro-6H-pyrido[2,3-b][1,4]benzodiazepin-6-one and 3-[4-[(acetyl)methylamino]-butyl]piperidine, but using dimethylformamide instead of acetonitrile as solvent. By dissolving the base in ethyl acetate and adding ethereal hydrochloric acid solution, the hydrochloride was obtained in a yield of 73% of theory.

IR (CH$_2$Cl$_2$): 1660 cm$^{-1}$ (C=O);
$^1$H-NMR (DMSO-d$^6$/CD$^3$OD; 80 MHz): delta : 8.3 (d, 1H); 7.9–7.3 (m, 6H); 4.2–2.5 (m, 10H); 2.1–1.0 (m, 14H).

MS: M$^+$: 463 m/e (corresponding to C$_{26}$H$_{33}$N$_5$O$_3$).

EXAMPLE 19

11-[[3-[3-[(Acetyl)methylamino]propyl-1-piperidinyl]-acetyl]-5,11-dihydro-6H-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 3-[3-[(acetyl)methylamino]-propyl]piperidine, but using dimethylformamide instead of acetonitrile as solvent, in a yield of 11% of theory.

Colourless crystals, m.p. 170°–172° C. (ethyl acetate).

EXAMPLE 20

11-[[3-[3-(Benzoyl)methylamino]propyl]-1-piperidinyl]-acetyl]-5,11-dihydro-6H-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 3-[3-[(benzoyl)methylamino]-propyl]piperidine in a yield of 61% of theory.

Colourless crystals, m.p. 172°–175° C. (ethyl acetate).

EXAMPLE 21

5,11-Dihydro-11-[[3-[3-[[b 2-(dimethylamino)ethyl]methylamino]propyl]-1-piperidinyl]acetyl]-6H-pyrido[2,3-b][1,4]-benzodiazepin-6-one Prepared analogously to Example 1 from 11-(chloroacetyl)-5,11-dihydro-6H-pyrido[2,3-b][1,4]benzodiazepin-6-one and 3-[3-[[2-(dimethylamino)ethyl]methylamino]-propyl]piperidine, but using dimethylformamide instead of acetonitrile as solvent, in a yield of 57% of theory.

RF=0.3 (methylene chloride/methanol/ammonia=50:10:1, v:v:v; Merck prepared TLC plates silica gel F-254).

IR (CH$_2$Cl$_2$) 3370 cm$^{-1}$ (N—H)
1680 cm$^{-1}$ (C=O)
1665 cm$^{-1}$ (C=O)

$^1$H-NMR (CDCl$_3$/CD$_3$OD; 400 MHz): delta : 8.4–7.3 (5H, aromat. H); 3.7–3.0 (2H, N—CO—CH$_2$—N); 3.0–2.1 (17H); 2.0–0.6 (13H).

MS: M$^+$: 478 m/e, calculated molecular weight: 478.6 g/mol.

EXAMPLE 22

11-[[3-[3-[3-(Diethylaminocarbonyl)-1-piperidinyl]-propyl]-1-piperidinyl]acetyl]-5,11-dihydro-6H-pyrido[2,3-b][1,4]-benzodiazepin-6-one Prepared analogously to Example 1 from 11-(chloroacetyl)-5,11-dihydro-6H-pyrido[2,3-b][1,4]benzodiazepin-6-one and 3-[3-[3-(diethylaminocarbonyl)-1-piperidinyl]-propyl]piperidine, but using dimethylformamide instead of acetonitrile as solvent, in a yield of 64% of theory.

IR (CH$_2$Cl$_2$): 1665, 1675 cm$^{-1}$ (C=O)
MS: M$^+$ 478.

EXAMPLE 23

5,11-Dihydro-11-[[3-[3-(1-piperidinyl)propyl]-1-piperidinyl]acetyl]-6H-pyrido [2,3-b][1,4]benzodiazepin-6-one Prepared analogously to Example 1 from 11-(chloroacetyl)-5,11-dihydro-6H-pyrido[2,3-b][1,4]benzodiazepin-6- one and 3-[3-(1-piperidinyl)propyl]piperidine, but using dimethylformamide instead of acetonitrile as solvent, in a yield of 42% of theory.

Colourless crystals, m.p. 192°–194° C. (diisopropylether).

EXAMPLE 24

5,11-Dihydro-11-[[4-[3-(1-piperidinyl)propyl]-1-piperidinyl]acetyl]- 6H-pyrido[2,3-b][1,4]benzodiazepin-6-one A mixture of 16.90 g (0.063 mol) of 4-[3-(1-piperidinyl)-propyl]piperidinoacetic acid and 2.0 g of a 75% sodium hydride dispersion in paraffin oil is heated in 160 ml of dimethylformamide at 50°–80° C. until the development of hydrogen has ended. To the resulting sodium salt of the above-mentioned acid are added 13.0 g (0.062 mol) of 5,11-dihydro-6H-pyrido[2,3-b][1,4]benzodiazepin- 6-one and at −10° C. 9.8 g (0.064 mol) of phosphorus oxychloride are added dropwise within 10 minutes. The resulting mixture is stirred for 4 hours at −10° C., for 4 hours at 0° C. and for 20 hours at ambient temperature. Then the mixture is stirred into 300 g of ice, adjusted to pH 9 with sodium hydroxide solution and extracted exhaustively with dichloromethane. The combined organic phases are washed once with a little ice water, dried over sodium sulphate and concentrated by evaporation. The residue is recrystallised from ethyl acetate using activated charcoal. Colourless crystals, m.p. 202°–203° C., totally identical to a sample obtained in Example 3 according to thin layer chromatography, mixed melting point, IR, UV and $^1$H-NMR spectra. Yield: 4.57 g (16% of theory).

EXAMPLE 25

4,9-Dihydro-4-[[4-[3-(dimethylamino)propyl]-1-piperidinyl]-acetyl]-3-methyl -10H-thieno[3,4-b][1,5]benzodiazepin- 10-one Prepared analogously to Example 1 from 4-(chloroacetyl)-4,9-dihydro-3-methyl-10H-thieno[3,4-b][1,5]benzodiazepin-10-one and 4-[3-(dimethylamino)propyl]piperidine in a yield of 27% of theory.

Colourless crystals, m.p. 196°–197° C. (ethyl acetate).

EXAMPLE 26

4-[[4-[3-(Diethylamino)propyl]-1-piperidinyl]acetyl]-4,9-dihydro-3-methyl-10H -thieno[3,4-b][1,5]benzodiazepin- 10-one Prepared analogously to Example 1 from 4-(chloroacetyl)-4,9-dihydro-3-methyl-10H-thieno[3,4-b][1,5]benzodiazepin-10-one and 4-[3-(diethylamino)propyl]piperidine in a yield of 32% of theory.

Colourless crystals, m.p. 209°–210° C. (t-butylmethylether).

EXAMPLE 27

4,9-Dihydro-3-methyl-4-[[4-[3-(1-piperidinyl)propyl]-1-piperidinyl]acetyl]-10H-thieno[3,4-b][1,5]benzodiazepin- 10-one Prepared analogously to Example 1 from 4-(chloroacetyl)-4,9-dihydro-3-methyl-10H-thieno[3,4-b][1,5]benzodiazepin-10-one and 4-[3-(1-piperidinyl)propyl]piperidine in a yield of 46% of theory.

Colourless crystals, m.p. 214°–215° C. (ethyl acetate).

EXAMPLE 28

11-[4-[3-(Diethylamino)propyl]-1-piperidinyl]acetyl]-6,11-dihydro-5H-pyrido [2,3-b][1,5]benzodiazepin-5-one Prepared analogously to Example 1 from 11-(chloroacetyl)-6,11-dihydro-5H-pyrido[2,3-b][1,5]benzodiazepin-5-one and 4-[3-(diethylamino)propyl]piperidine in a yield of 24% of theory.

Colourless crystals, m.p. 168°–169° C. (ethyl acetate).

EXAMPLE 29

4,9-Dihydro-3-methyl-4-[[4-[4-(1-piperidinyl)butyl]-1-piperidinyl]acetyl]-10H-thieno[3,4-b][1,5]benzodiazepin- 10-one Prepared analogously to Example 1 from 4-(chloroacetyl)-4,9-dihydro-3-methyl-10H-thieno[3,4-b][1,5]benzodiazepin-10-one and 4-[4-(1-piperidinyl)butyl]piperidine in a yield of 50% of theory.

Colourless crystals, m.p. 195°–197° C. (ethyl acetate).

EXAMPLE 30

11-[[4-[4-(Diethylamino)butyl]-1-piperidinyl]acetyl]-5,11-dihydro-6H-pyrido [2,3-b][1,4]benzodiazepin-6-one Prepared analogously to Example 1 from 11-(chloroacetyl)-5,11-dihydro-6H-pyrido[2,3-b][1,4]benzodiazepin-6-one and 4-[4-(diethylamino)butyl]piperidine in a yield of 43% of theory.
Colourless crystals, m.p. 155°-156° C.

EXAMPLE 31

5,11-Dihydro-11-[[4-[3-(1-methyl-2-pyrrolidinyl)-propyl]-1-piperidinyl]acetyl]-6H-pyrido[2,3-b][1,4]benzodiazepin- 6-one Prepared analogously to Example 1 from 11-(chloroacetyl)-5,11-dihydro-6H-pyrido[2,3-b][1,4]benzodiazepin-6-one and 4-[3-(1-methyl-2-pyrrolidinyl)-propyl]piperidine in a yield of 32% of theory.
Colourless crystals, m.p. 207°-209° C. (acetonitrile).

EXAMPLE 32

11-[[4-[5-(Diethylamino)pentyl -1-piperidinyl]acetyl]-5,11-dihydro-6H-pyrido [2,3-b][1,4]benzodiazepin-6-one Prepared analogously to Example 1 from 11-(chloroacetyl)-5,11-dihydro-6H-pyrido[2,3-b][1,4]benzodiazepin-6-one and 4-[5-(diethylamino)pentyl]piperidine in a yield of 21% of theory.
Colourless crystals, m.p. 137°-138° C. (ethyl acetate).

EXAMPLE 33 trans-4,9-Dihydro-4-[[4-[3-[(4-hydroxycyclohexyl) methylamino]propyl]- 1-piperidinyl]acetyl -3-methyl-10H-thieno[3,4-b][1,5]benzodiazepin-10-one Prepared analogously to Example 1 from 4-(chloroacetyl)-4,9-dihydro-3-methyl-10H-thieno[3,4-b][1,5]benzodiazepin-6-one and trans-4-[3-[(4-hydroxycyclohexyl)methylamino]-propyl]piperidine in a yield of 10% of theory.
Colourless crystals, m.p. 150°-151° C. (ethyl acetate/dichloromethane 3:1 v/v).

EXAMPLE 34

4,9-Dihydro-3-methyl-4-[[4-[3-(4-methyl-1-piperazinyl)-propyl]-1-piperidinyl]acetyl]-10H-thieno[3,4-b][1,5-benzodiazepin-10-one Prepared analogously to Example 1 from 4-(chloroacetyl)-4,9-dihydro-3-methyl-10H-thieno[3,4-b][1,5]benzodiazepin-10-one and 4-[3-(4-methyl-1-piperazinyl)propyl]piperidine in a yield of 40% of theory.
Colourless crystals, m.p. 217°-218° C. (ethyl acetate).

EXAMPLE 35

11-[[2-[2-[2-(Diethylamino)ethoxy]ethyl]-1-piperidinyl]-acetyl]-5,11-dihydro-6H-pyrido[2,3-b][1,4]benzodiazepin- 6-one Prepared analogously to Example 1 from 11-(chloroacetyl)-5,11-dihydro-6H-pyrido[2,3-b][1,4]benzodiazepin-6- one and 2-[2-[2-(diethylamino)ethoxy]ethyl]piperidine (Bp.0.4 mmHg 95°-99° C.) in a yield of 44% of theory.
Colourless crystals. m.p. 102°-104° C. (recrystallised from diisopropylether and cyclohexane).

EXAMPLE 36

11-[[4-[2-[2-(Diethylamino)ethoxy]ethyl]-1-piperidinyl]-acetyl]-5,11-dihydro-6H-pyrido[2,3-b][1,4]benzodiazepin-6-one Prepared analogously to Example 1 from 11-(chloroacetyl)-5,11-dihydro-6H-pyrido[2,3-b][1,4]benzodiazepin-6-one and 4-[2-[2-(diethylamino)ethoxy]ethyl]piperidine (Bp0.009 mmHg 96°-102° C.) in a yield of 46% of theory.
Colourless crystals, m.p. 130°-131° C. (acetonitrile).

EXAMPLE 37

9-Chloro-11-[[4-[2-[2-(diethylamino)ethoxy]ethyl]-1-piperidinyl]acetyl]-5,11-dihydro-6H-pyrido[2,3-b][1,4]-benzodiazepin-6-one Prepared analogously to Example 1 from 9-chloro-11-(chloroacetyl)- 5,11-dihydro-6H-pyrido[2,3-b][1,4]benzodiazepin-6- one and 4-[2-[2-(diethylamino) ethoxy]ethyl]piperidine in a yield of 35% of theory.
Colourless crystals, m.p. 165.5°-166.5° C. (acetonitrile/n-propanol 3:1 v/v).

EXAMPLE 38

3-Chloro-4-[[4-[4-(diethylamino)butyl]-1-piperidinyl-acetyl]-1-methyl-1,4,9,10-tetrahydropyrrolo[3,2-b][1,5]-benzodiazepin-10-one Prepared analogously to Example 1 from 3-chloro-4-(chloroacetyl)-1-methyl-1,4,9,10-tetrahydropyrrolo-[3,2-b][1,5]benzodiazepin - 10-one and 4-[4-(diethylamino)butyl]piperidine in a yield of 34% of theory.
Colourless crystals, m.p. 158°-160° C.

EXAMPLE 39

4-[[4-[4-(Diethylamino)butyl]-1-piperidinyl]acetyl]-1-methyl-1,4,9,10-tetrahydropyrrolo [3,2-b][1,5]benzodiazepin-10-one 3.957 g (8.14 millimol) of 3-chloro-4-[[4-[4-(diethylamino)-butyl]-1-piperidinyl]acetyl ]-1-methyl-1,4,9,10-tetrahydropyr rolo[3,2-b][1,5]benzodiazepin-10-one were dissolved in 350 ml of hot ethanol and after the addition of 3 g of palladium on animal charcoal (20%), hydrogenated for 20 hours under a hydrogen pressure of 50 bar and at a temperature of 40° C. The catalyst was filtered off, the filtrate was concentrated by evaporation in vacuo, the crystalline hydrochloride was taken up in 20 ml of water, the solution obtained was made alkaline with sodium hydroxide and extracted exhaustively with dichloromethane. The combined extracts were dried over sodium sulphate and evaporated down and the residue remaining was recrystallised. 1 g (26.3% of theory) of colourless crystals were obtained, m.p. 198° C. (acetonitrile).

EXAMPLE 40

4-[[4-[4-(Diethylamino)butyl]-1-piperidinyl]acetyl]-1-methyl-1,4,9,10-tetrahydropyrrolo [3,2-b][1,5]benzodiazepin-10-one 4.715 g (9.7 millimol) of 3-chloro-4-[[4-[4-(diethylamino)-butyl]-1-piperidinyl]acetyl ]-1-methyl-1,4,9,10-tetrahydropyr rolo[3,2-b][1,5]benzodiazepin-10-one were dissolved in a mixture of 5 ml of 85% formic acid and 25 ml of dimethylformamide and after the addition of 0.5 g of 10% palladium/activated charcoal the mixture was refluxed for 3 hours. 7.0 ml of formic acid were added, the mixture was refluxed for a further 6 hours and then, after the addition of a further 4.0 ml of formic acid and 0.8 g of 10% palladium/activated charcoal, the mixture was finally refluxed for a further 8 hours. The mixture was filtered while hot, the filtrate was evaporated down in vacuo and the residue was purified by column chromatography (silica gel; dichloromethane/ethyl acetate/methanol/conc. ammonia 3.5:1.5:0.46:0.06 v/v). 1.45 g (33% of theory) of colourless crystals were obtained, m.p. 196°-198° C. (acetonitrile), which were found according to thin layer chromatography and IR, UV and $^1$H-NMR spectra, to be identical to a preparation obtained according to Example 39.

EXAMPLE 41

4-[[4-[4-(Diethylamino)butyl]-1-piperidinyl]acetyl]-1-methyl-1,4,9,10-tetrahydropyrrolo[3,2-b][1,5]benzodiazepin-10-one A mixture of 4.86 g (0.01 mol) of 3-chloro-4-[[4-[4-(diethylamino)butyl]-1-piperidinyl]acetyl]-1-methyl-1,4,9,10-tetrahydropyrrolo[3,2-b][1,5]benzo- diazepin-10-one 83.3 mg (0.001 mol) of 2:1-tris(o-tolyl)-phosphine/palladium acetate catalyst, 2.025 g (0.044 mol) of formic acid and 5.77 g (0.057 mol) of triethylamine in 200 ml of tetrahydrofuran was heated to 100° C. in an autoclave for 40 hours under a nitrogen atmosphere. The mixture was filtered and evaporated down in vacuo, the residue was made alkaline with sodium hydroxide and extracted exhaustively with dichloromethane. After drying and evaporation, the organic phases were purified by column chromatography as in Example 40. 1.76 g (3% of theory) of colourless crystals were obtained, m.p. 196°-198° C. (acetonitrile), which were found according to thin layer chromatography and IR spectrum to be identical to a sample obtained according to Example 39.

The following Examples illustrate the preparation of some pharmaceutical administration forms:

EXAMPLE I

Tablets containing 5 mg of 4,9-dihydro-3-methyl-4-[[4-[3-(1-piperidinyl)propyl]-1-piperidinyl]acetyl]-10H-thieno[3,4-b][1,5]benzodiazepin- 10-one

| Composition: | |
|---|---|
| 1 tablet contains: | |
| Active substance | 5.0 mg |
| Lactose | 148.0 mg |
| Potato starch | 65.0 mg |
| Magnesium stearate | 2.0 mg |
| | 220.0 mg |

Method of Preparation

A 10% mucilage is prepared from potato starch by heating. The active substance, lactose and remaining potato starch are mixed together and granulated with the above mucilage through a 1.5 mm mesh screen. The granules are dried at 45° C., rubbed through the same screen again, mixed with magnesium stearate and compressed to form tablets.

| Weight of tablet: | 220 mg |
|---|---|

-continued

| Punch: | 9 mm |
|---|---|

EXAMPLE II

Coated tablets containing 5 mg of 4,9-dihydro-3-methyl-4-[[4-[3-(1-piperidinyl)propyl]-1-piperidinyl]acetyl]-10H-thieno[3,4-b][1,5]benzodiazepin-10-one The tablets prepared according to Example I are coated, by a known method, with a coating consisting essentially of sugar and talc. The finished coated tablets are polished with beeswax.

Weight of coated tablet: 300 mg

EXAMPLE III

Ampoules containing 10 mg of 4,9-dihydro-3-methyl-4-[[4-[3-(1-piperidinyl)propyl]-1-piperidinyl]acetyl]-10H-thieno[3,4-b][1,5]benzodiazepin-10-one

| Composition: | |
|---|---|
| 1 ampoule contains: | |
| Active substance | 10.0 mg |
| Sodium chloride | 8.0 mg |
| Distilled water ad | 1 ml |

Method of Preparation

The active substance and sodium chloride are dissolved in distilled water and then made up to the volume specified. The solution is sterile filtered and transferred into 1 ml ampoules.

Sterilisation: 20 minutes at 120° C.

Example IV

Suppositories containing 20 mg of 4,9-dihydro-3-methyl- 4-[[4-[3-(1-piperidinyl)propyl]-1-piperidinyl]acetyl]-10H-thieno[3,4-b][1,5]benzodiazepin-10-one

| Composition: | |
|---|---|
| 1 suppository contains: | |
| Active substance | 20.0 mg |
| Suppository mass (e.g. Witepsol W 45$^{(R)}$) | 1680.0 mg |
| | 1700.0 mg |

Method of Preparation

The finely powdered active substance is suspended in the molten suppository mass which has been cooled to 40° C. The mass is poured at 37° C. into slightly chilled suppository moulds.

Weight of suppository 1.7 g.

EXAMPLE V

Drops containing 4,9-dihydro-3-methyl-4-[[4-[3-(1-piperidinyl)-propyl]-1-piperidinyl]acetyl]-10H-thieno-[3,4-b][1,5]benzodiazepin-10-one

| Composition: |
|---|
| 100 ml of drops solution contain: |

-continued

| Composition: | |
|---|---|
| Methyl p-hydroxybenzoate | 0.035 g |
| Propyl p-hydroxybenzoate | 0.015 g |
| Anisole | 0.05 g |
| Menthol | 0.06 g |
| Pure ethanol | 10.0 g |
| Active substance | 0.5 g |
| Sodium cyclamate | 1.0 g |
| Glycerol | 15.0 g |
| Distilled water ad | 100.0 ml |

Method of Preparation

The active substance and sodium cyclamate are dissolved in about 70 ml of water and glycerol is added. The p-hydroxybenzoates, anisole and menthol are dissolved in ethanol and this solution is added with stirring to the aqueous solution. Finally, the solution is made up to 100 ml with water and filtered to remove any suspended particles.

What is claimed is:

1. A diazepinone of formula

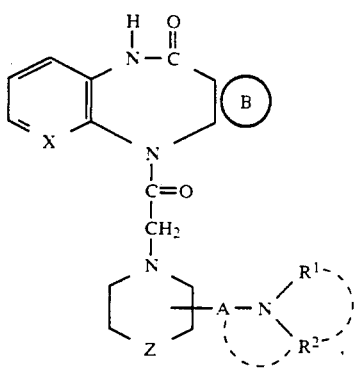 (I)

wherein Ⓑ represents one of the divalent groups

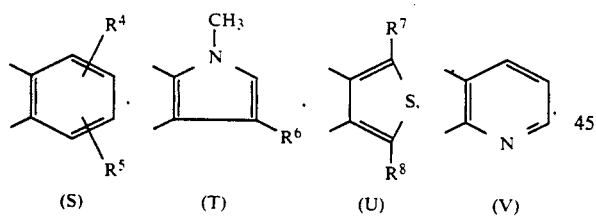

X is a =CH— group or a nitrogen atom,
A is a straight-chained or branched, saturated $C_3$-$C_7$ alkylene group which may also be interrupted by an oxygen or sulphur atom or the group >NR3, wherein R3 is a $C_1$-$C_3$ alkyl group
Z is a single bond, an oxygen or sulphur atom, a methylene or 1,2-ethylene group,
$R^1$ is a branched or unbranched $C_1$-$C_7$ alkyl group, a cycloalkyl or (cycloalkyl)alkyl group with a total of up to 8 carbon atoms, an aralkyl group with up to 9 carbon atoms optionally substituted by a fluorine, chlorine or bromine atom and/or by a methyl, methoxy or trifluoromethyl group, an aliphatic acyl group with up to 7 carbon atoms or a benzoyl group optionally substituted by a fluorine, chlorine or bromine atom and/or by a methyl, methoxy or trifluoromethyl group,
$R^2$ represents a branched or unbranched $C_1$-$C_6$ alkyl group, but $R^2$ may also be a hydrogen atom if $R^1$ represents the above-mentioned aliphatic acyl group or optionally substituted benzoyl group,
$R^1$ and $R^2$ may also, together with the nitrogen atom between them, represent a saturated, monocyclic 5-, 6- or 7-membered ring which optionally may also be substituted by an aminocarbonyl, dimethylaminocarbonyl or diethylaminocarbonyl group and/or may be interrupted by an oxygen atom,
$R^2$ may also, however, be linked to a carbon atom of the A chain in such a way that, together with the group $NR^1$, a saturated 5-, 6- or 7-membered heterocyclic ring is formed,
$R^4$ and $R^5$, which may be identical or different, represent a hydrogen, fluorine, chlorine or bromine atom or an alkyl group with 1 to 4 carbon atoms,
$R^6$ is a hydrogen or chlorine atom or a methyl group,
$R^7$ and $R^8$, which may be identical or different, represent hydrogen atoms or $C_1$-$C_4$ alkyl groups, but $R^8$ may also represent a halogen atom,
the diastereoisomeric and enantiomeric forms thereof, or a physiologically acceptable salt with inorganic or organic acid.

2. The diazepinone as recited in claim 1 wherein the group

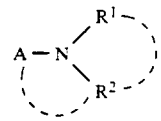

is in the 3- or 4- position of the saturated heterocyclic group and
A · represents a straight-chained or branched $C_3$-$C_5$ alkylene group which may optionally be interrupted by the group >N—CH3,
X represents a nitrogen atom or a =CH— group,
B represents the divalent group (S) or (U), wherein $R^4$ and $R^5$ represent hydrogen atoms, $R^7$ and $R^8$ represent hydrogen atoms or one of these groups represents the methyl group,
$R^1$ and $R^2$, which may be identical or different, represent $C_1$-$C_3$ alkyl groups or together with the nitrogen atom between them represent the 1-piperidinyl group or $R^2$ together with the corresponding carbon atom of the group —A— represents the 4-piperidinyl group of formula

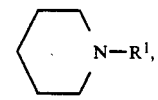

wherein $R^1$ represents a $C_1$-$C_3$ alkyl group and Z represents the methylene group,
the diastereoisomeric and enantiomeric forms thereof or a physiologically acceptable salt with inorganic or organic acid.

3. The diazepinone as recited in claim 1, 5,11-Dihydro-11-[[4-[4-(1-piperidinyl)butyl]-1-piperidinyl]acetyl]-6H-pyrido[2,3-b][1,4]benzodiazepin-6-one and a physiologically acceptable salt thereof with inorganic or organic acid.

4. The diazepinone as recited in claim 1, 5,11-Dihydro-11-[[4-[3-(1-methyl-4-piperidinyl)-propyl]-1-piperidinyl]acetyl]-6H-pyrido[2,3-b][1,4]-benzodiazepin-6-one and a physiologically acceptable salt thereof with inorganic or organic acid.

5. The diazepinone as recited in claim 1, 5,11-Dihydro-11-[[4-[3-(1-piperidinyl)propyl]- 1-piperidinyl-]acetyl]-6H-pyrido[2,3-b][1,4]benzodiazepin- 6-one and a physiologically acceptable salt thereof with inorganic or organic acid.

6. The diazepinone as recited in claim 1, 4,9-Dihydro-3-methyl-4-[[4-[3-(1-piperidinyl)propyl]-1-piperidinyl]-acetyl]-10H-thieno[3,4-b][1,5]benzodiazepin- 10-one and a physiologically acceptable salt thereof with inorganic or organic acid.

7. A pharmaceutical composition comprising a diazepinone of formula

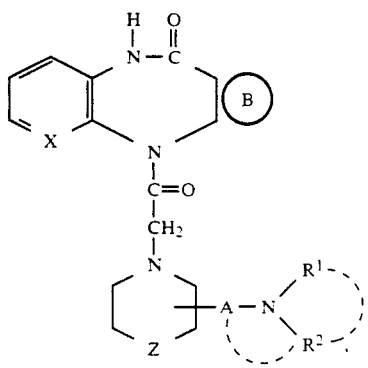
(I)

wherein B represents one of the divalent groups

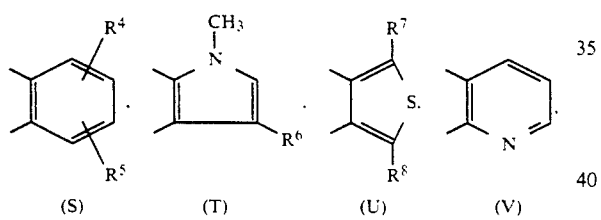

X is a =CH— group or a nitrogen atom,

A is a straight-chained or branched, saturated $C_3$-$C_7$ alkylene group which may also be interrupted by an oxygen or sulphur atom or the group NR3, wherein R3 is a $C_1$-$C_3$ alkyl group Z is a single bond, an oxygen or sulphur atom, a methylene or 1,2-ethylene group, $R^1$ is a branched or unbranched $C_1$-$C_7$ alkyl group, a cycloalkyl or (cycloalkyl)alkyl group with a total of up to 8 carbon atoms, an aralkyl group with up to 9 carbon atoms optionally substituted by a fluorine, chlorine or bromine atom and/or by a methyl, methoxy or trifluoromethyl group, an aliphatic acyl group with up to 7 carbon atoms or a benzoyl group optionally substituted by a fluorine, chlorine or bromine atom and/or by a methyl, methoxy or trifluoromethyl group, $R^2$ represents a branched or unbranched $C_1$-$C_6$ alkyl group, but $R^2$ may also be a hydrogen atom if $R^1$ represents the above-mentioned aliphatic acyl group or optionally substituted benzoyl group, $R^1$ and $R^2$ may also, together with the nitrogen atom between them, represent a saturated, monocyclic 5-, 6- or 7-membered ring which optionally may also be substituted by an aminocarbonyl, dimethylaminocarbonyl or diethylaminocarbonyl group and/or may be interrupted by an oxygen atom, $R^2$ may also, however, be linked to a carbon atom of the A chain in such a way that, together with the group $NR^1$, a saturated 5-, 6- or 7-membered heterocyclic ring is formed, $R^4$ and $R^5$, which may be identical or different, represent a hydrogen, fluorine, chlorine or bromine atom or an alkyl group with 1 to 4 carbon atoms, $R^6$ is a hydrogen or chlorine atom or a methyl group, $R^7$ and $R^8$, which may be identical or different, represent hydrogen atoms or $C_1$-$C_4$ alkyl groups, but $R^8$ may also represent a halogen atom, the diastereoisomeric and enantiomeric forms thereof, or a physiologically acceptable salt with inorganic or organic acid and a pharmaceutically acceptable carrier.

8. A method for treatment of bradycardia in a warm-blooded animal which comprises administering to said animal a therapeutically effective amount of a diazepinone of formula

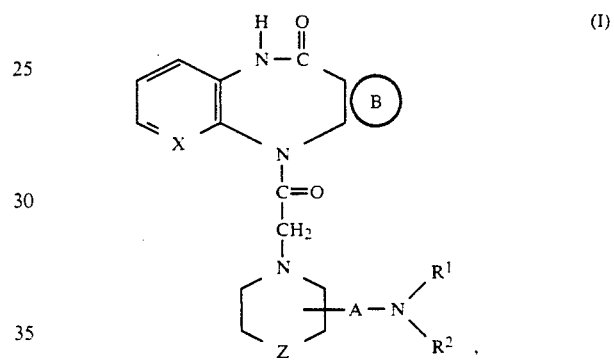
(I)

wherein B represents one of the divalent groups

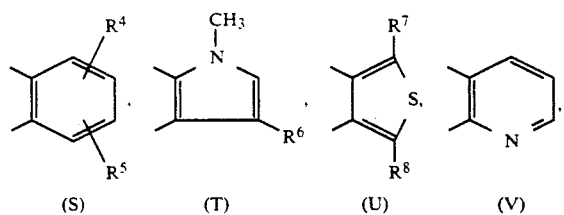

X is a =CH— group or a nitrogen atom,

A is a straight-chained or branched, saturated $C_3$-$C_7$ alkylene group which may also be interrupted by an oxygen or sulphur atom or the group NR3, wherein R3 is a $C_1$-$C_3$ alkyl group Z is a single bond, an oxygen or sulphur atom, a methylene or 1,2-ethylene group, $R^1$ is a branched or unbranched $C_1$-$C_7$ alkyl group, a cycloalkyl or (cycloalkyl)alkyl group with a total of up to 8 carbon atoms, an aralkyl group with up to 9 carbon atoms optionally substituted by a fluorine, chlorine or bromine atom and/or by a methyl, methoxy or trifluoromethyl group, an aliphatic acyl group with up to 7 carbon atoms or a benzoyl group optionally substituted by a fluorine, chlorine or bromine atom and/or by a methyl, methoxy or trifluoromethyl group, $R^2$ represents a branched or unbranched $C_1$-$C_6$ alkyl group, but $R^2$ may also be a hydrogen atom if $R^1$ represents the above-mentioned aliphatic acyl group or optionally substituted benzoyl group, R¹ and R² may also, together with the nitrogen atom between them, represent a saturated, monocyclic 5-, 6- or 7-membered ring which optionally may also be substituted by an aminocarbonyl, dimethylaminocarbonyl or diethylaminocarbonyl group and/or may be interrupted by an oxygen atom, R² may also, however, be linked to a carbon atom of the A chain in such a way that, together with the group NR¹, a saturated 5-, 6- or 7-membered heterocyclic ring is formed, R⁴ and R⁵, which may be identical or different, represent a hydrogen, fluorine, chlorine or bromine atom or an alkyl group with 1 to 4 carbon atoms, R⁶ is a hydrogen or chlorine atom or a methyl group, R⁷ and R⁸, which may be identical or different, represent hydrogen atoms or C₁-C₄ alkyl groups, but R⁸ may also represent a halogen atom, the diastereoisomeric and enantiomeric forms thereof, or a physiologically acceptable salt with inorganic or organic acid and a pharmaceutically acceptable carrier.

9. A method for treatment of bradyarrhythmia in a warm-blooded animal which comprises administering to said animal a therapeutically effective amount of a diazepinone of formula

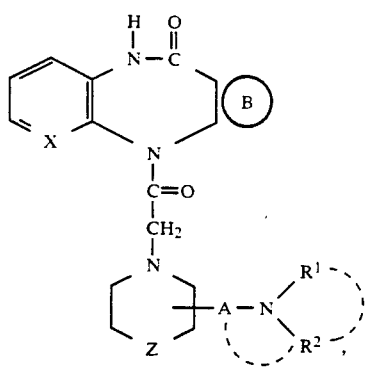

wherein B represents one of the divalent groups

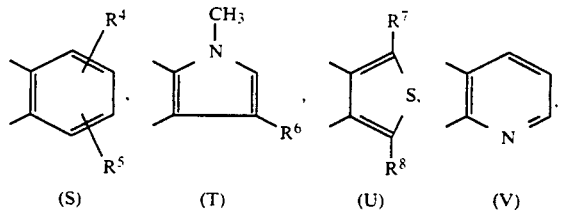

X is a =CH— group or a nitrogen atom,

A is a straight-chained or branched, saturated C₃-C₇ alkylene group which may also be interrupted by an oxygen or sulphur atom or the group NR3, wherein R3 is a C₁-C₃ alkyl group Z is a single bond, an oxygen or sulphur atom, a methylene or 1,2-ethylene group, R¹ is a branched or unbranched C₁-C₇ alkyl group, a cycloalkyl or (cycloalkyl)alkyl group with a total of up to 8 carbon atoms, an aralkyl group with up to 9 carbon atoms optionally substituted by a fluorine, chlorine or bromine atom and/or by a methyl, methoxy or trifluoromethyl group, an aliphatic acyl group with up to 7 carbon atoms or a benzoyl group optionally substituted by a fluorine, chlorine or bromine atom and/or by a methyl, methoxy or trifluoromethyl group, R² represents a branched or unbranched C₁-C₆ alkyl group, but R² may also be a hydrogen atom if R¹ represents the above-mentioned aliphatic acyl group or optionally substituted benzoyl group, R¹ and R² together with the nitrogen atom between them, represent a saturated, monocyclic 5-, 6- or 7-membered ring which optionally may also be substituted by an aminocarbonyl, dimethylaminocarbonyl or diethylaminocarbonyl group and/or may be interrupted by an oxygen atom, R² may also, however, be linked to a carbon atom of the A chain in such a way that, together with the group NR¹, a saturated 5-, 6- or 7-membered heterocyclic ring is formed, R⁴ and R⁵, which may be identical or different, represent a hydrogen, fluorine, chlorine or bromine atom or an alkyl group with 1 to 4 carbon atoms, R⁶ is a hydrogen or chlorine atom or a methyl group, R⁷ and R⁸, which may be identical or different, represent hydrogen atoms or C₁-C₄ alkyl groups, but R⁸ may also represent a halogen atom, the diastereoisomeric and enantiomeric forms thereof, or a physiologically acceptable salt with inorganic or organic acid and a pharmaceutically acceptable carrier.

* * * * *